(12) United States Patent
Lu et al.

(10) Patent No.: US 10,428,132 B2
(45) Date of Patent: Oct. 1, 2019

(54) TUMOR NECROSIS FACTOR-RELATED APOPTOSIS-INDUCING LIGAND VARIANT, AS WELL AS A PREPARATION METHOD AND USE THEREOF

(71) Applicant: WEST CHINA HOSPITAL, SICHUAN UNIVERSITY, Chengdu, Sichuan (CN)

(72) Inventors: XiaoFeng Lu, Sichuan (CN); Hao Yang, Sichuan (CN); Lin Wan, Sichuan (CN); JingQiu Cheng, Sichuan (CN)

(73) Assignee: WEST CHINA HOSPITAL, SICHUAN UNIVERSITY, Chengdu, Sichuan (CN)

(*) Notice: Subject to any disclaimer, the term of this patent is extended or adjusted under 35 U.S.C. 154(b) by 135 days.

(21) Appl. No.: 15/501,623

(22) PCT Filed: Feb. 11, 2015

(86) PCT No.: PCT/CN2015/072787
§ 371 (c)(1),
(2) Date: Feb. 3, 2017

(87) PCT Pub. No.: WO2016/127346
PCT Pub. Date: Aug. 18, 2016

(65) Prior Publication Data
US 2017/0305987 A1 Oct. 26, 2017

(51) Int. Cl.
*C07K 14/525* (2006.01)
*C07K 19/00* (2006.01)
(Continued)

(52) U.S. Cl.
CPC ...... *C07K 14/525* (2013.01); *C07K 14/70575* (2013.01); *A61K 38/00* (2013.01); *C07K 2319/33* (2013.01)

(58) Field of Classification Search
None
See application file for complete search history.

(56) References Cited

U.S. PATENT DOCUMENTS 9,102,759 B2 * 8/2015 Pieczykolan .... C07K 14/70575
9,340,596 B2 * 5/2016 Hua ................... C07K 14/7151
2015/0044162 A1 2/2015 Pieczykolan et al.

FOREIGN PATENT DOCUMENTS

CN 101717449 A 6/2010
CN 102775497 A 11/2012
(Continued)

OTHER PUBLICATIONS

Ashkenazi et al., Safety and antitumor activity of recombinant soluble Apo2 ligand, J Clin Invest. 104(2):155-162, Jul. 15, 1999.*
(Continued)

*Primary Examiner* — Claire Kaufman
(74) *Attorney, Agent, or Firm* — Novick, Kim & Lee, PLLC; Allen Xue

(57) ABSTRACT

The present invention discloses a tumor necrosis factor-related apoptosis-inducing ligand variant, which is a fusion protein of a tumor necrosis factor-related apoptosis-inducing ligand and an F3 peptide. The F3 peptide is fused to the N-terminus or C-terminus of the tumor necrosis factor-related apoptosis-inducing ligand by a linker. The present invention also discloses a nucleotide sequence, as well as a recombinant vector and a recombinant bacterium comprising same, and also discloses a preparation method and use of the foregoing variant.

18 Claims, 9 Drawing Sheets
Specification includes a Sequence Listing.

(51) Int. Cl.
*C07K 14/705* (2006.01)
*A61K 38/19* (2006.01)
*A61K 38/00* (2006.01)

(56) References Cited

FOREIGN PATENT DOCUMENTS

| | | | |
|---|---|---|---|
| CN | 102863537 A | 1/2013 | |
| CN | 102958940 A | 3/2013 | |
| CN | 103228788 A | 7/2013 | |
| CN | 103237808 A | 8/2013 | |
| CN | 103987728 A | 8/2014 | |
| WO | 03087124 A2 | 10/2003 | |

OTHER PUBLICATIONS

DrugBank Database, Dulanermin. [Retrieved online Aug. 3, 2018]. Retrieved from:internet URL: DrugBank, https://www.drugbank.ca/drugs/DB12349>, 2018.*

Cate et al., A novel AML-selective TRAIL fusion protein that is superior to Gemtuzumab Ozogamicin in terms of in vitro selectivity, activity and stability, Leukemia, 23(8):1389-1397, Aug. 2009.*

Henke et al., A novel AML-selective TRAIL fusion protein that is superior to Gemtuzumab Ozogamicin in terms of in vitro selectivity, activity and stability, Nat. Biotech. 26(1):91-100, 2008.*

Chen et al., Fusion protein linkers: property,design and functionality, Adv. Drug Deliv. Rev. 65:1357-1369, 2013.*

Wang et al., RGD and NGR modified TRAIL protein exhibited potent anti-metastasis effects on TRAIL-insensitive cancer cells in vitro and in vivo, Amino Acids, 49:931-941, 2017.*

Hartung et al., Guided TRAIL to cancer cells through Kv10.1 potassium channel overcomes resistance to doxorubicin, Eur. Biophys. J.45:709-719, 2016.*

Cao et al, "Enhancement of antitumor properties of TRAIL by targeted delivery to the tumor neovasculature," Mol Cancer Ther, 7(4): 851-861, Apr. 15, 2008.*

Anel et al.,APO2L/TRAIL: new insights in the treatment of autoimmune disorders, Recent Pat. Inflamm. Allergy Drug Discov. 5(3): 184-99, Sep. 2011.*

Ralf Bieker et al., Infarction of tumor vessels by NGR-peptide-directed targeting of tissue factor: experimental results and first-in-man experience, Bloodjournal, Jan. 3, 2015, 5019-5027, vol. 113 No. 20, The American Society of Hematology.

F. Gonzalvez and A Ashkenazi, New insights into apoptosis signaling by Apo2L/TRAIL, npg, Jun. 7, 2010, 4752-4765, Oncogene, Macmillan.

Hira Lal Goel and Arthur M. Mercurio, VEGF targets the tumour cell, Nature Reviews, Dec. 2013, 871-881, Macmillan.

Kimmo Porkka et al., A fragment of the HMGN2 protein homes to the nuclei of tumor cells and tumor endothelial cells in vivo, PNAS, May 28, 2002, 7444-7449, vol. 99 No. 11.

Soria JC. Mark Z. Zatloukal P. et al., Randomized Phase II Study of Dulanermin in Combination with Paclitaxel, Carboplatin, and Bevacizumab in Advanced Non-Small-Cell Lung Cancer, J Clin Oncol, 2011, 4442-4451, vol. 29.

Daniel W. Stuckey and Khalid Shah, TRAIL on Trial: Preclinical advances for cancer therapy, Trends Mol Med., Nov. 2013, 1-20, 19(11).

Vivek Subbiah et al., Targeting the Apoptotic Pathway in Chondrosarcoma Using Recombinant Human Apo2L/TRAIL (Dulanermin), a Dual Proapoptotic Receptor (DR4/DR5) Agonist, Molecular Cancer Therapeutics, Nov. 2012, 2541-2546, 11(11), American Association for Cancer Research.

Nicholas S. Wilson et al., Proapoptotic Activation of Death Receptor 5 on Tumor Endothelial Cells Disrupts the Vasculature and Reduces Tumor Growth, Cancer Cell Article, Jul. 10, 2012, 80-90, 22, Elsevier Inc.

* cited by examiner

TUMOR NECROSIS FACTOR-RELATED APOPTOSIS-INDUCING LIGAND VARIANT, AS WELL AS A PREPARATION METHOD AND USE THEREOF

INCORPORATION OF SEQUENCE LISTING

This application contains a sequence listing submitted in Computer Readable Form (CRF). The CFR file containing the sequence listing entitled "PA288-0010-seq1_v3.txt", which was created on Nov. 16, 2018, and is 12,892 bytes in size. The information in the sequence listing is incorporated herein by reference in its entirety.

FIELD OF THE INVENTION

The present invention relates to the field of genetic engineering, and in particular to a tumor necrosis factor-related apoptosis-inducing ligand variant, as well as a preparation method and use thereof.

BACKGROUND OF THE INVENTION

Cancer is one of the main diseases threatening human life. Surgery, radiotherapy and chemotherapy are currently the main means of cancer treatment. Drugs which are able to penetrate into tumors and kill tumor cells with less damage to normal cells are ideal for chemotherapy. However, most traditional chemotherapeutic drugs lack the selectivity in killing cells. With the in-depth understanding of the molecular mechanism of tumorigenesis and tumor progression, and the discovery of tumor markers, drugs for targeting therapies have become a new trend in the development of tumor chemotherapeutic drugs (Nero T L et al. Nat Rev Cancer. 2014, 14: 248-62; Goel H L et al. Nat Rev Cancer. 2013, 13: 871-82).

A tumor necrosis factor-related apoptosis-inducing ligand (TRAIL) is a member of the tumor necrosis factor (TNF) superfamily. The full-length molecule consists of 281 amino acids, including the N-terminal hydrophobic transmembrane domain and the C-terminal hydrophilic extracellular domain. TRAIL has four membrane-bound receptors (TRAIL R1, R2, R3 and R4) and a soluble receptor (OPG). Of these receptors, only TRAIL R1 and R2 are death receptors (DRs). Once bound to TRAIL, the DRs on the cell membrane could be activated followed by induction of apoptosis. However, TRAIL R3 and R4 receptors are both decoy receptors (DcRs), which do not trigger apoptosis upon ligand engagement. The death receptors TRAIL R1 and R2 are overexpressed in tumor cells, whereas the decoy receptors R3 and R4 are overexpressed in normal cells. Thus, TRAIL can induce tumor apoptosis, sparing normal cells (Gonzalvez F et al. Oncogene. 2010, 29: 4752-65). Both in vitro and in vivo studies demonstrate that human soluble TRAIL produced by genetic engineering displays potent killing effects cytotoxicity in breast cancer, colon cancer, lung cancer, prostate cancer, kidney cancer, bladder cancer, liver cancer, osteosarcoma, chondroma, lymphoma, neuroblastoma, hematological tumors (Stucke D W et al. Trends Mol Med. 2013, 19(11): 685-94; Wilson N S et al. Cancer Cell. 2012, 22(1): 80-90). Human soluble TRAIL has entered clinical trial phase I-II as an anti-tumor drug. It was found that TRAIL was well tolerated, and patients with a variety of tumors showed response to the treatment of TRAIL suggesting that TRAIL might be developed as a novel anti-cancer drug (Subbiah V et al. Mol Cancer Ther. 2012, 11(11): 2541-6. Soria J C et al. J Clin Oncol. 2011, 29(33): 4442-51).

However, the clinical anti-tumor efficacy of this format of soluble TRAIL is still unsatisfactory, mainly due to the wide distribution of its decoy receptors and poor targeting for tumors. The tumor-targeting of TRAIL might be enhanced by fusing TRAIL to antibodies or tumor-homing peptides that can specifically bind tumor cells, so as to further improve the anti-tumor effects of TRAIL in vivo.

The F3 peptide consists of amino acids 17-48 of a human high mobility group nucleosomal binding protein 2, which is capable of specifically binding to tumor cells and tumor vascular endothelial cells (Porkka K et al. Proc. Natl. Acad. Sci. USA. 2002, 99 (11): 7444-9), and enhancing the targeting properties of certain anti-tumor drugs. However, the F3 peptide has not been reported to be used to enhance the tumor-targeting of TRAIL so as to further improve its anti-tumor activity.

SUMMARY OF THE INVENTION

In order to solve the above problems, the present invention provides a tumor necrosis factor-related apoptosis-inducing ligand variant, namely a TRAIL variant, as well as a preparation method and use thereof.

The present invention relates to a tumor necrosis factor-related apoptosis-inducing ligand variant, which is a fusion protein comprising a tumor necrosis factor-related apoptosis-inducing ligand and an F3 peptide. The F3 peptide was fused to the N-terminus or C-terminus of the tumor necrosis factor-related apoptosis-inducing ligand by a linker, wherein the amino acid sequence of said tumor necrosis factor-related apoptosis-inducing ligand is as shown in SEQ ID NO: 2, and wherein the amino acid sequence of said F3 peptide is as shown in SEQ ID NO: 4. Preferably, said F3 peptide is encoded by the nucleotide sequence as shown in SEQ ID NO: 3, wherein said linker consists of 2-20 amino acids. Preferably, said linker is a (G4S)$_3$ linker and the amino acid sequence thereof is as shown in SEQ ID NO: 6, wherein said tumor necrosis factor-related apoptosis-inducing ligand variant is encoded by the nucleotide sequence as shown in SEQ ID NO: 7 or 9. The amino acid sequence of said tumor necrosis factor-related apoptosis-inducing ligand variant is as shown in SEQ ID NO: 8 or 10.

The present invention relates to a nucleotide sequence comprising the coding sequence of the tumor necrosis factor-related apoptosis-inducing ligand and the coding sequence of the F3 peptide, both of which are linked by the coding sequence of the linker, wherein the coding sequence of said tumor necrosis factor-related apoptosis-inducing ligand is as shown in SEQ ID NO: 1, wherein the coding sequence of said F3 peptide is as shown in SEQ ID NO: 3, and wherein said linker is a (G4S)$_3$ linker, and the nucleotide sequence thereof is as shown in SEQ ID NO: 5.

Said nucleotide sequence is as shown in SEQ ID NO: 7 or 9.

The present invention also provides a recombinant vector or a recombinant bacterium comprising the foregoing nucleotide sequence.

The present invention relates to a method for preparing the foregoing tumor necrosis factor-related apoptosis-inducing ligand variant. The variant is prepared by means of genetic engineering with the foregoing nucleotide sequence as a target fragment.

The present invention also provides the use of the foregoing tumor necrosis factor-related apoptosis-inducing ligand variant in the preparation of a drug for treating cell proliferative diseases, wherein said drug for treating cell proliferative diseases is a drug for treating tumors or autoimmune diseases.

The present invention also provides an anti-tumor drug which is a preparation prepared by adding pharmaceutically acceptable adjuvants to the foregoing tumor necrosis factor-related apoptosis-inducing ligand variant as an active ingredient.

At present, one of the approaches for improving the anti-tumor activity of protein drugs in the art is to enhance the tumor targeting property by fusing targeting peptides to anti-tumor proteins. The key problem is the newly added targeting peptide and the original protein drug may affect each other thus could not exhibit their original functions. If so, the activity of the new protein might not be stronger than that of the original protein. At present, there are numerous tumor-targeting peptides, such as those of the RGD family and NGR family. It is not clear which targeting peptide is proper for enhancement of the activity of original protein. The activity of the new fusion proteins might vary with the types of the peptides and the sites for fusion. For example, Bieker et al. (Blood 2009; 113: 5019-5027) enhanced the anti-tumor activity of a tissue factor by fusing L-NGR targeting peptide having the amino acid sequence as SEQ ID NO: 15 at its N-terminus. However, the present inventor found that the N-terminal fusion of L-NGR targeting peptide did not enhanced anti-tumor activity of TRAIL, demonstrating the uncertainty of the use of the tumor-targeting peptide for improving the anti-tumor activity of protein drugs.

In the present invention, after the nucleotide sequence being optimized, the F3 targeting peptide was fused to TRAIL to prepare a fusion protein that displaying better tumor-targeting property. Both in vivo and in vitro experiments demonstrate that the anti-tumor effect of the fusion protein is better than that of TRAIL in tumors, especially in TRAIL-resistant tumors, which could not be predicted by any technical way.

In the present invention, pure TRAIL variant proteins including TRAIL-F3-C and TRAIL-F3-N have been prepared by genetic engineering. The cytotoxicity of both proteins in tumor cells is significantly stronger than that of TRAIL. Especially, the TRAIL variant protein TRAIL-F3-N is obviously superior to TRAIL in terms of affinity for tumor cells, stability, apoptosis-inducing ability in tumor cells, tumor-targeting property, and in vivo anti-tumor effect. Especially, the TRAIL variant protein TRAIL-F3-N can suppress the growth of TRAIL-resistant tumors, suggesting the potentials of TRAIL-F3-N in clinical application.

A. Fusion to F3 enhances the cytotoxicity of TRAIL in tumor cells. B. The fusion of random control peptide PC to TRAIL does not enhance the cytotoxicity of TRAIL in tumor cells.

Figure 5:
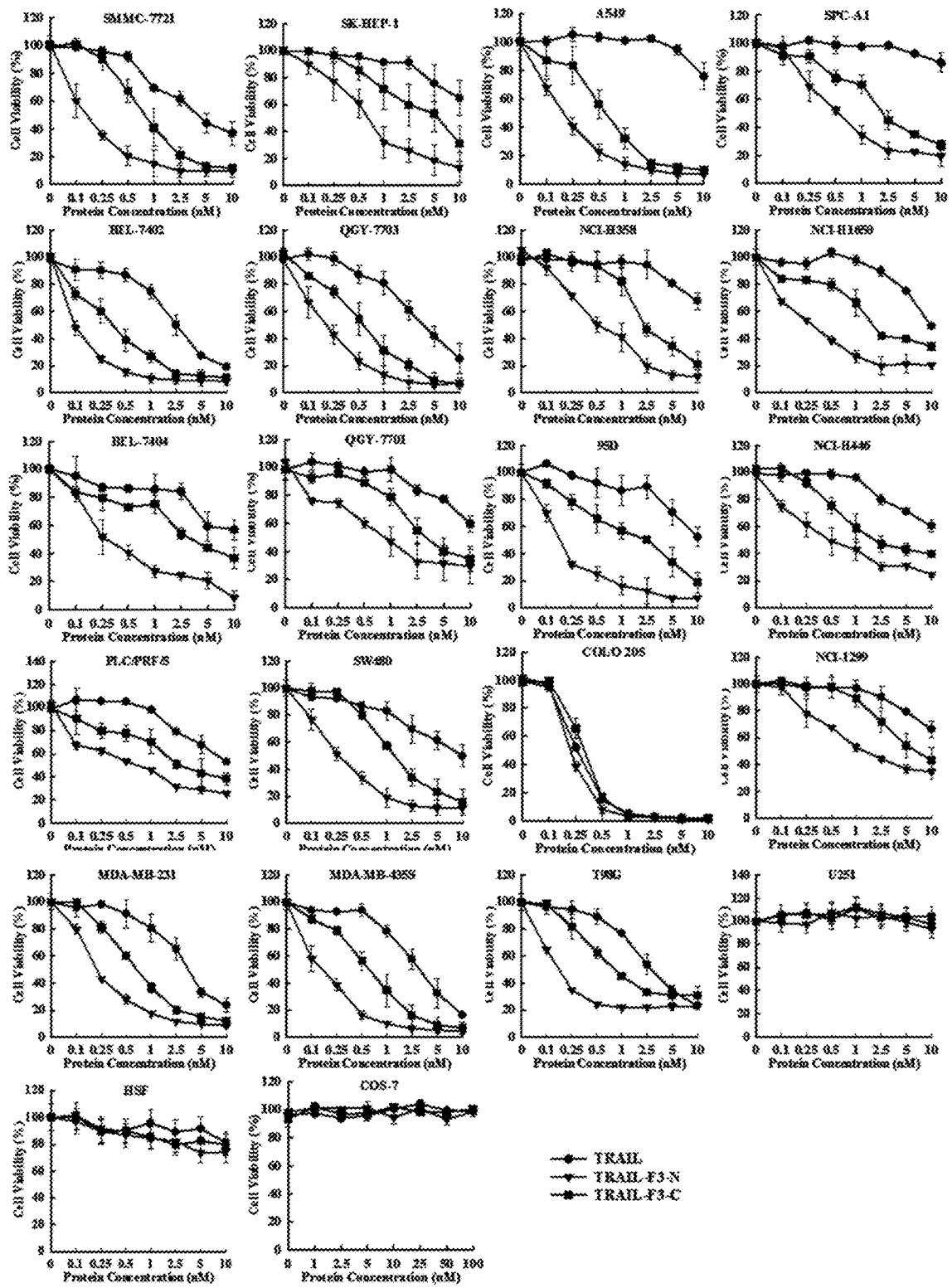

FIG. 5. Comparison of cytotoxicity of TRAIL variant proteins and TRAIL.

Figure 6:
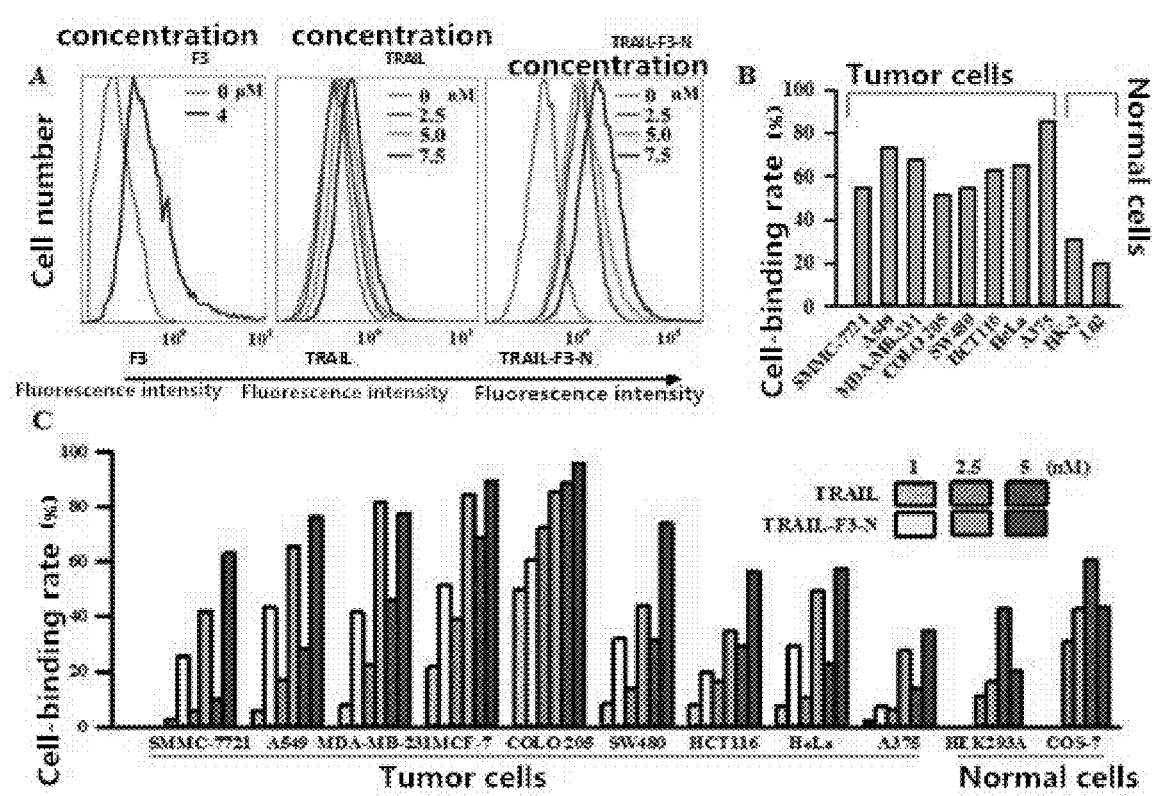

FIG. 6. Comparison of cell-binding capacity of TRAIL variant proteins and TRAIL.

A. The binding capacity of F3, TRAIL and TRAIL-F3-N to tumor cell SMMC-7721. B. Comparison of binding rates of F3 (4 µM) to tumor cells and to normal cells. C. Comparison of binding rates of TRAIL and TRAIL-F3-N to tumor cells and to normal cells.

Figure 7:
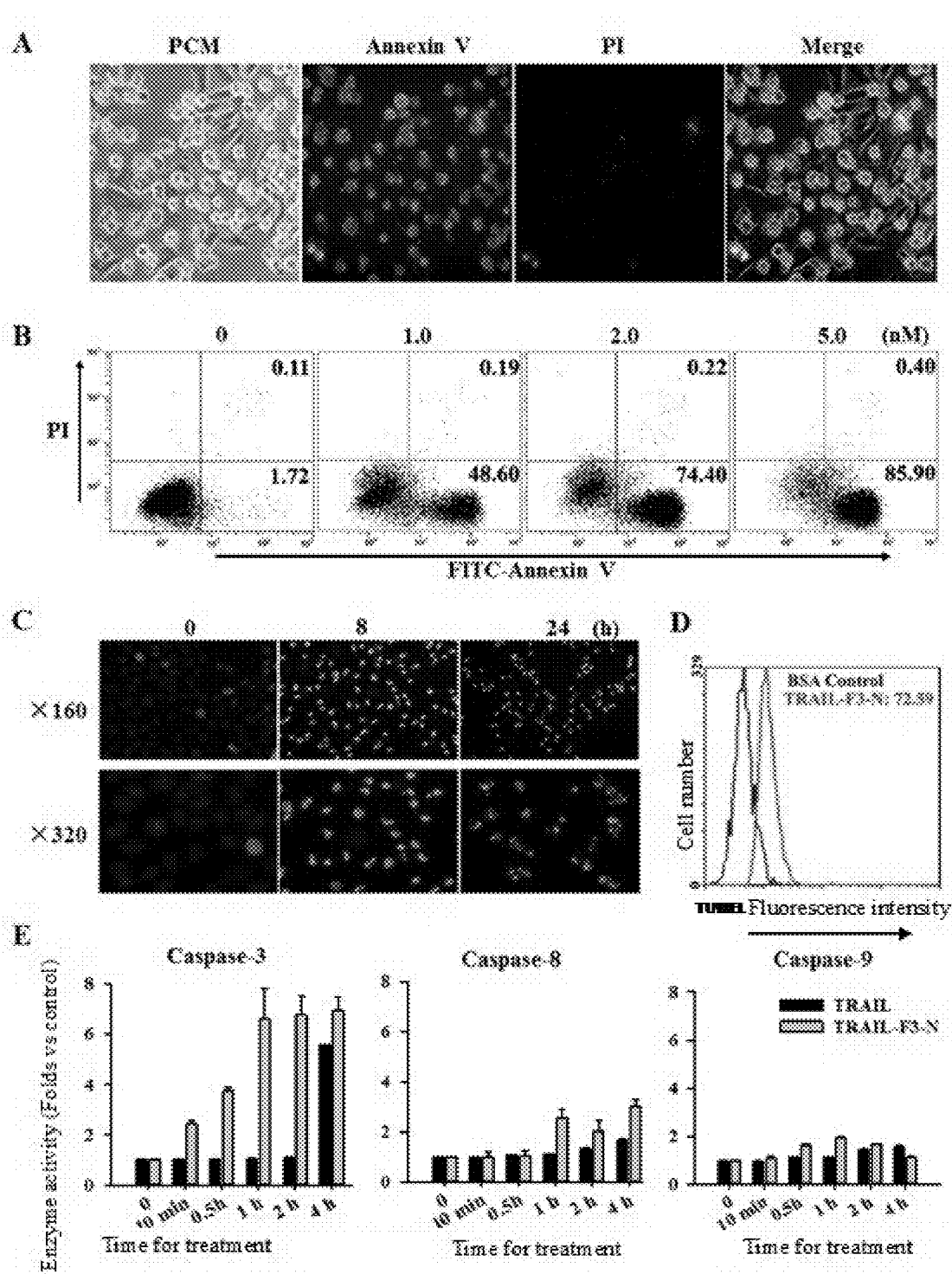

FIG. 7. TRAIL variant protein induces apoptosis in tumor cells. A and B. Annexin V (green fluorescence)/PI (red fluorescence) staining combined with fluorescence microscope observation (A) and flow cytometry analysis (B) Detection of TRAIL-F3-N-induced apoptosis in SMMC-7721 cells. C and D. Nuclear morphological changes (C) and DNA fragmentation (TUNEL positive cell percentage (D) after the treatment of SMMC-7721 cells with TRAIL-F3-N. E. TRAIL-F3-N and TRAIL induce the activation of Caspase-3, 8, 9 in SMMC-7721 cells.

Figure 8:
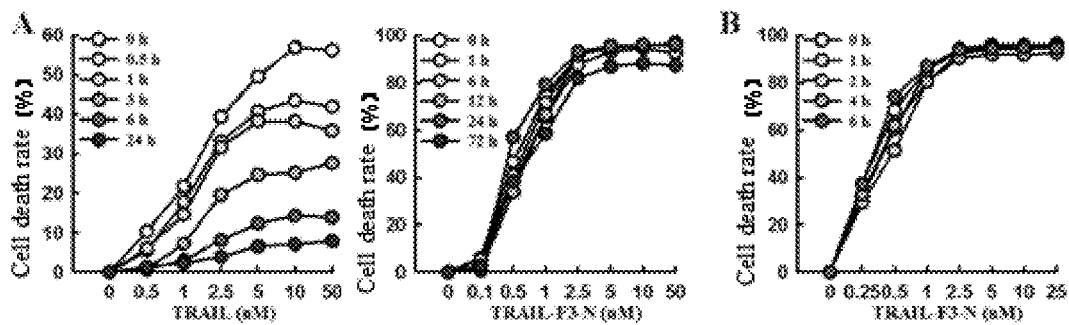

FIG. 8. Stability of TRAIL variant proteins in plasma (A) and whole blood (B).

Figure 9:
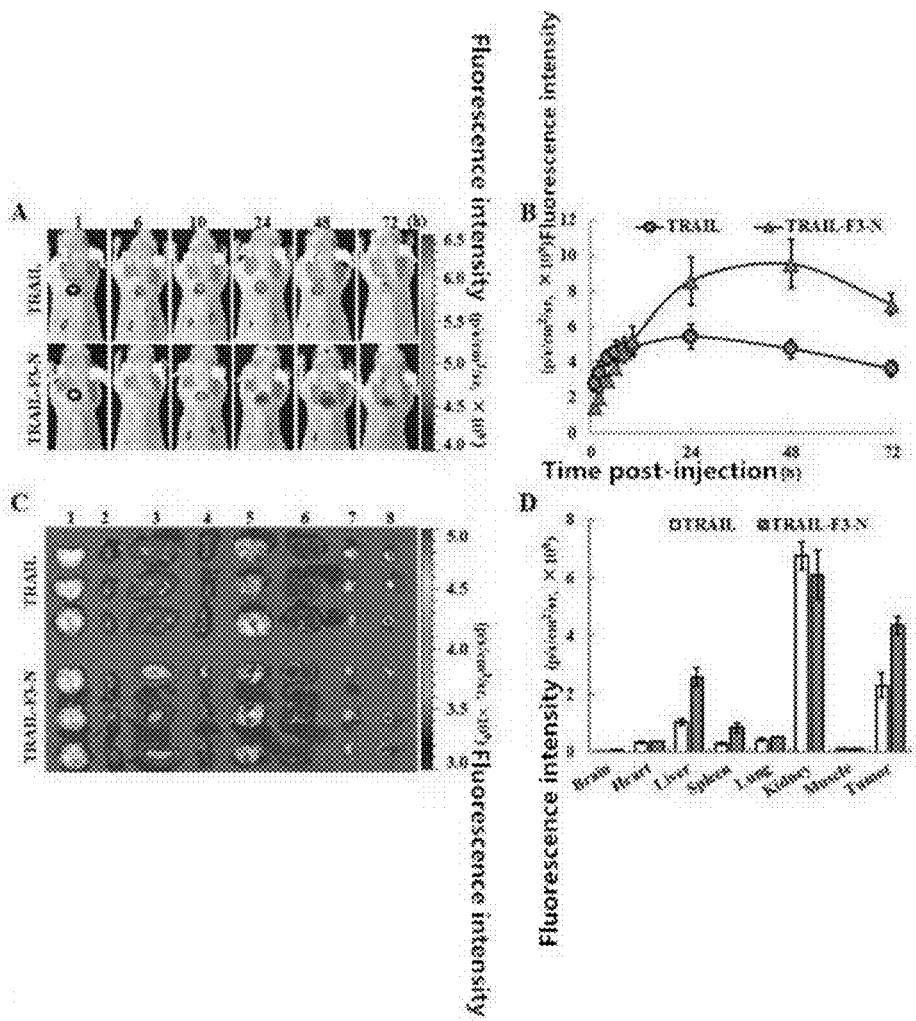

FIG. 9. Tumor-targeting property and tissue distribution of TRAIL variant proteins in vivo. A. In vivo imaging shows the uptakes of TRAIL-F3-N and TRAIL by tumors (circle indicated). B. Comparison on tumor uptakes of TRAIL-F3-N and TRAIL. C. Tissue distribution of TRAIL-F3-N and TRAIL. 1: Brain; 2: Heart; 3: Liver; 4: Spleen; 5: Lung; 6: Kidney; 7: Muscle; 8: Tumor. D. Comparison of contents of TRAIL-F3-N and TRAIL in different tissues.

Figure 10:
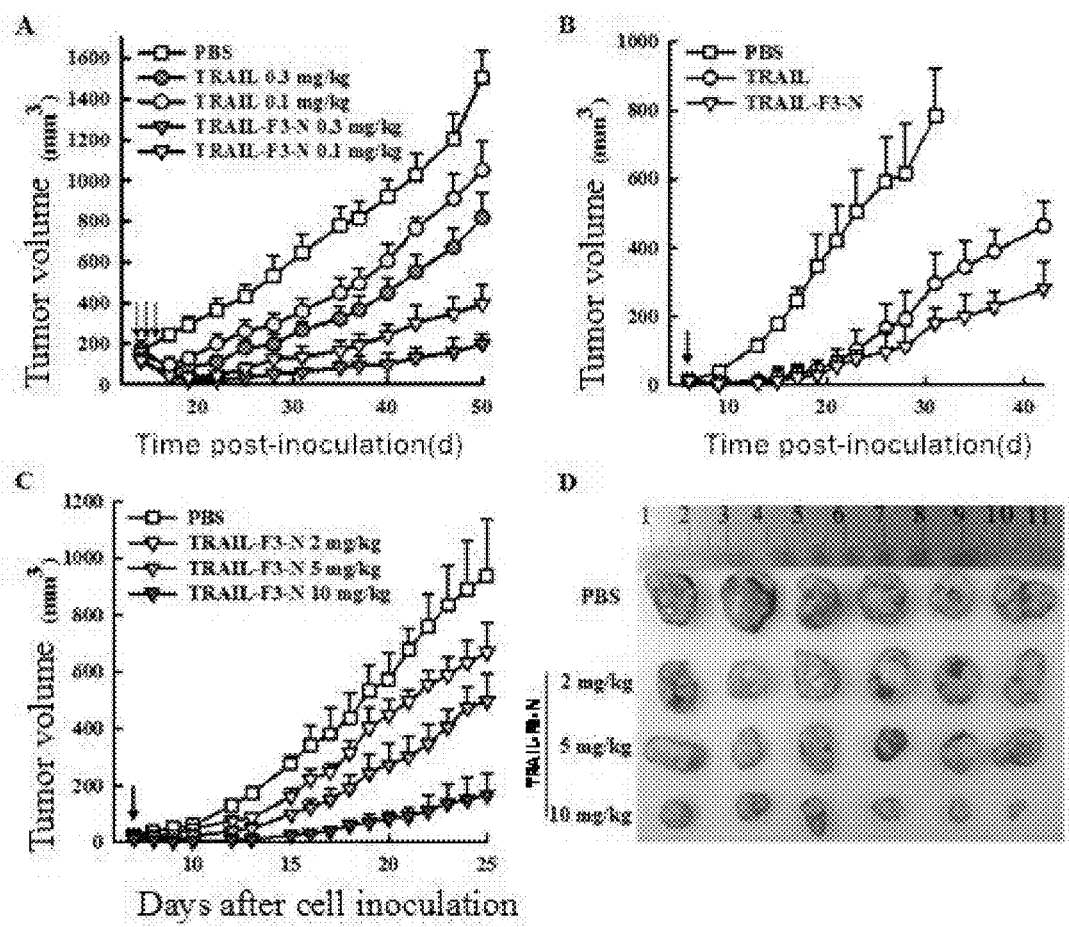

FIG. 10. In vivo anti-tumor effect of TRAIL variants on mice bearing TRAIL-sensitive COLO 205 tumor xenografts.

A. Tumor growth suppression mediated by intratumorally injected TRAIL-F3-N and TRAIL (n=7). B. Tumor growth suppression mediated by intravenously injected TRAIL-F3-N and TRAIL (n=7). C. Tumor growth suppression mediated by intravenously injected TRAIL-F3-N at different doses (n=6). D. Comparison of the size of tumors in each group at the end of experiment described in Figure C. The dosing time was indicated by arrow.

Figure 11:
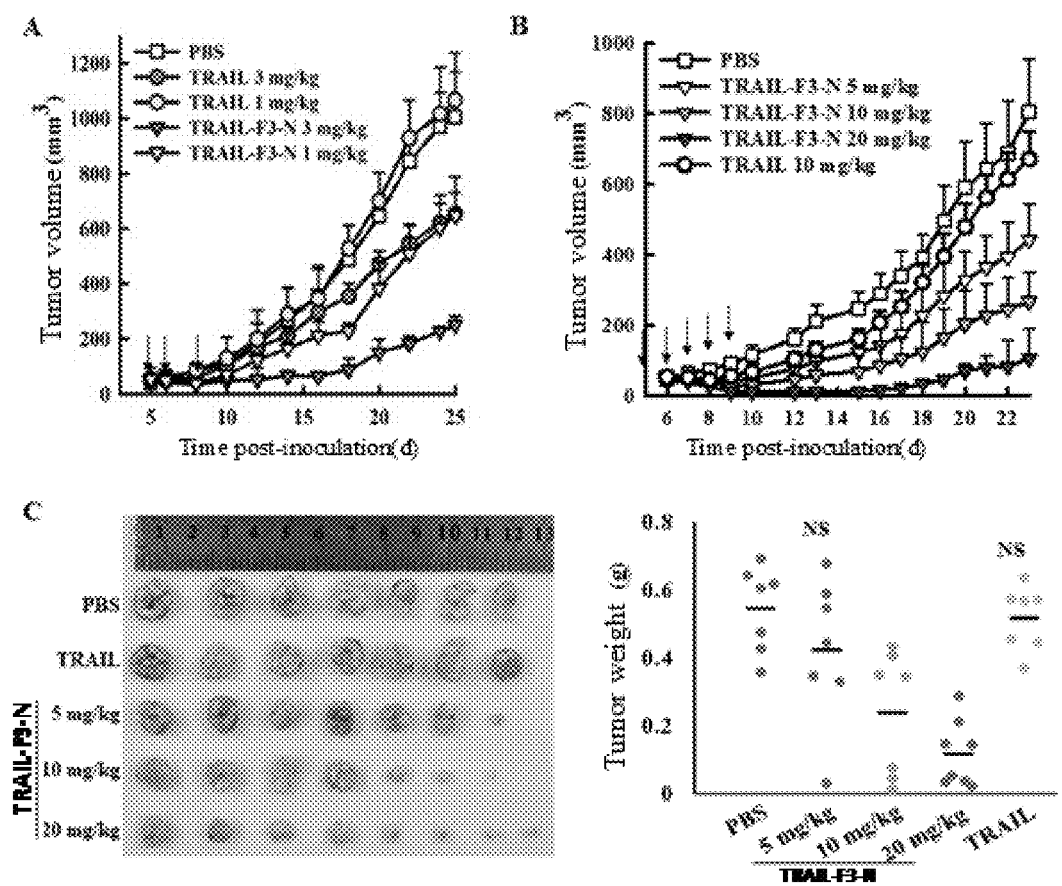

FIG. 11. In vivo anti-tumor effect of TRAIL variant proteins on mice bearing TRAIL-resistant A549 tumor xenografts.

A. Tumor growth suppression mediated by intratumorally injected TRAIL-F3-N and TRAIL (n=6). B. Tumor growth suppression mediated by intravenously injected TRAIL-F3-N and TRAIL (n=7-8). C. Comparison of size and weight of tumors in each group at the end of the experiment described in Figure B.

Figure 12:
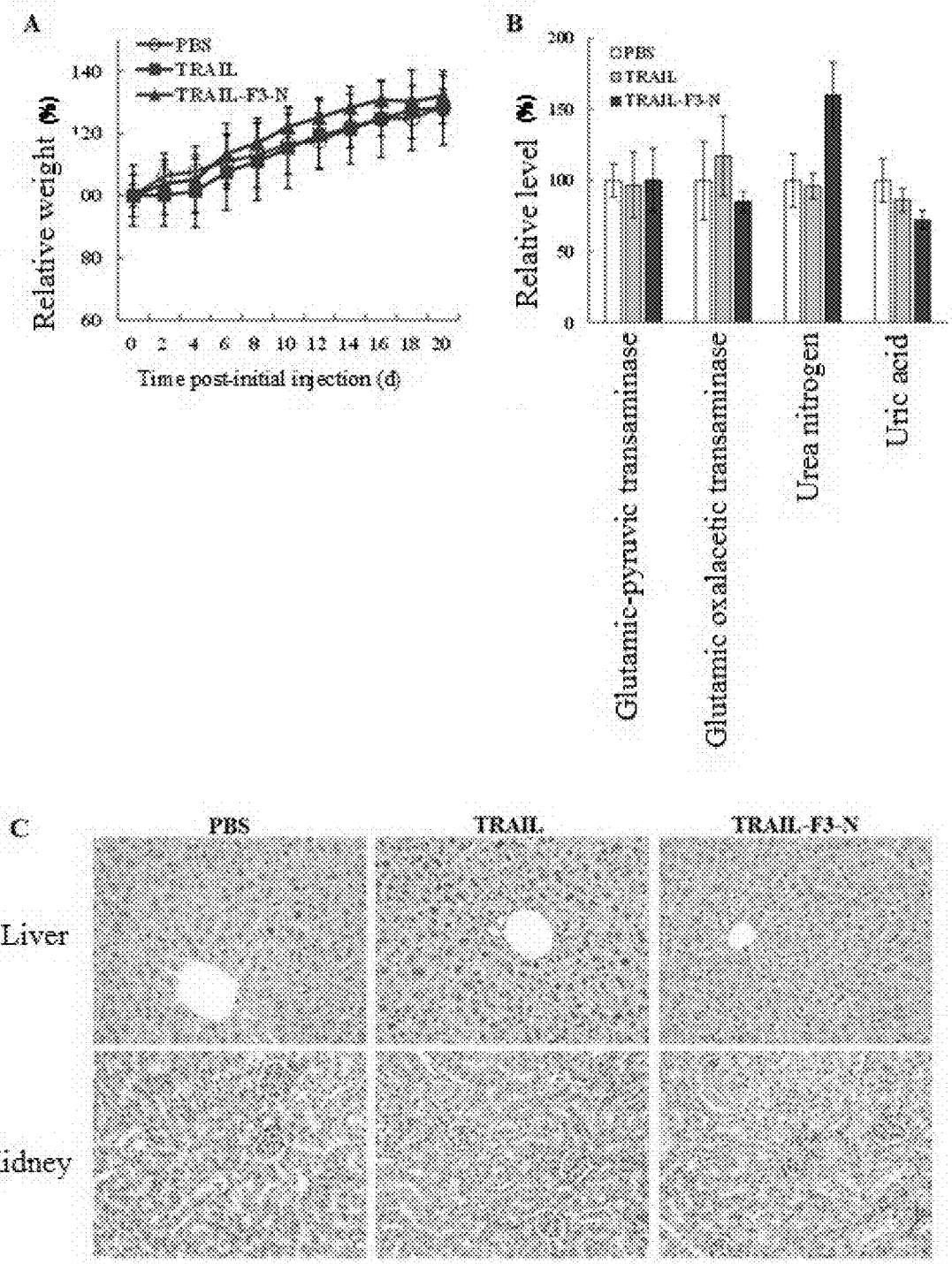

FIG. 12. Short-term acute toxicity evaluation of TRAIL variant protein. A. Mice body weight changing curve during administration. B. Blood biochemical indexes for liver and kidney functions of mice at the end of the administration. ALT: glutamic-pyruvic transaminase; AST: glutamic oxaloacetic transaminase; UREAL: urea; UA: uric acid. C. Histological examination of liver and kidney of mice at the end of administration.

SPECIFIC EMBODIMENTS

The above-mentioned contents of the present invention will be further described in detail below by specific embodiments in the form of examples. However, this should not be construed as limiting the scope of the above-mentioned subject of the present invention to the following examples. All techniques achieved based on the above-mentioned contents of the present invention fall within the scope of the present invention.

Example 1 Preparation of TRAIL Variants of the Present Invention

1. Design and Gene Cloning of TRAIL Variants
1) Design of TRAIL Variants

Figure 1:
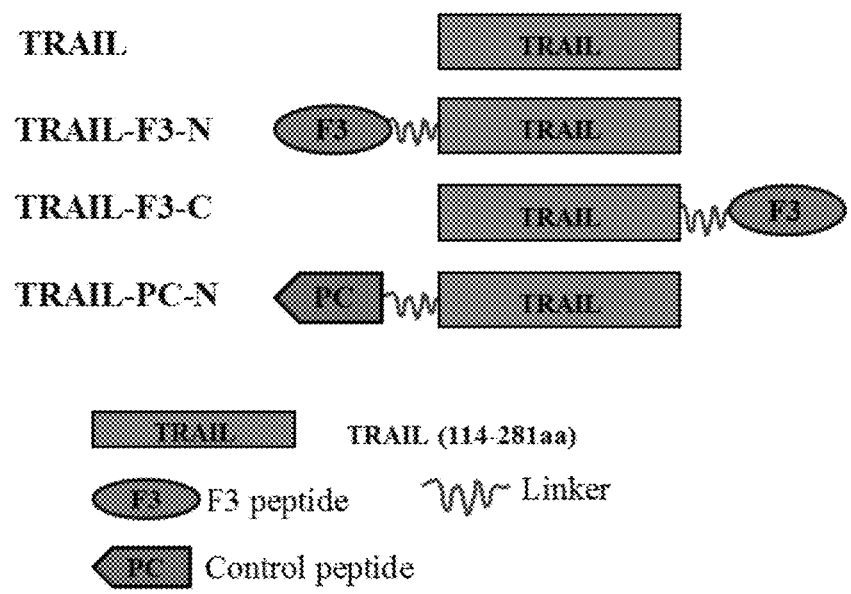
FIG. 1. Schematical structure of the fusion proteins.

The F3 peptide consists of 31 amino acids. TRAIL is a fragment composed of the amino acids 114-281 of human TRAIL. F3 could be fused to the N-terminus or C-terminus of TRAIL. And a flexible linker, such as $(G4S)_3$, could be inserted between the two segments. As shown in FIG. 1, the fusion proteins produced by the fusing F3 to the N-terminus or C-terminus of TRAIL were designated as TRAIL-F3-N and TRAIL-F3-C, respectively. At the same time, the control peptide PC was fused to the N-terminus of TRAIL to produce TRAIL-PC-N.

According to the molecular design, the gene encoding F3 or PC was genetically fused to TRAIL by using DNA analysis software. Subsequently, genes encoding TRAIL-F3-N, TRAIL-F3-C and TRAIL-PC-N were synthesized by Genscript Company (Nanjing, China)

TABLE 1

The present invention relates to amino acid sequences and nucleic acid sequences

| Name | Sequences |
|---|---|
| F3 peptide sequence (SEQ ID NO: 4) | KDEPQRRSARLSAKPAPPKPEPKPKKAPAKK |
| F3 nucleic acid sequence (SEQ ID NO: 3) | Aaggatgaaccacagagaagatccgcgcgtctttctgctaaacctgctcctccaaagccagagc ccaagcctaagaaagcccctgcaaagaaa |
| TRAIL114-281 amino acid sequence (SEQ ID NO: 2) | VRERGPQRVAAHITGTRGRSNTLSSPNSKNEKALGRKINSWES SRSGHSFLSNLHLRNGELVIHEKGFYYIYSQTYFRFQEEIKENT KNDKQMVQYIYKYTSYPDPILLMKSARNSCWSKDAEYGLYSI YQGGIFELKENDRIFVSVTNEHLIDMDHEASFFGAFLVG |
| TRAIL114-281 nucleic acid sequence (SEQ ID NO: 1) | Gtgagagaaagaggtcctcagagagtagcagctcacataactgggaccagaggaagaagcaa cacattgtcttctccaaactccaagaatgaaaaggctctgggccgcaaaataaactcctgggaatc atcaaggagtgggcattcattcctgagcaacttgcacttgaggaatggtgaactggtcatccatgaa aaagggttttactacatctattcccaaacatactttcgatttcaggaggaaataaagaaaacaaa gaacgacaaacaaatggtccaatatatttacaaatacacaagttatcctgaccctatattgttgatgaa aagtgctagaaatagttgttggtctaaagatgcagaatatggactctattccatctatcaaggggaa tatttgagcttaaggaaaatgacagaattttttgtttctgtaacaaatgagcacttgatagacatggacc atgaagccagttttttcggggccttttagttggc |
| PC peptide sequence | STVQEKQQNISPL |
| Nucleic acid sequence of PC peptide | Agcactgttcaagagaaacaacagaatattagtccgctg |
| G4S linker (SEQ ID NO: 6) | GGGGSGGGGSGGGGS |
| G4S nucleic acid sequence (SEQ ID NO: 5) | Ggtggaggcggttcaggcggaggtggctctggcggtggcggatcg |
| TRAIL-F3-N amino acid sequence (SEQ ID NO: 8) | KDEPQRRSARLSAKPAPPKPEPKPKKAPAKKGGGGSGGGGSG GGGSVRERGPQRVAAHITGTRGRSNTLSSPNSKNEKALGRKIN SWESSRSGHSFLSNLHLRNGELVIHEKGFYYIYSQTYFRFQEEI KENTKNDKQMVQYIYKYTSYPDPILLMKSARNSCWSKDAEY GLYSIYQGGIFELKENDRIFVSVTNEHLIDMDHEASFFGAFLVG |
| TRAIL-F3-N nucleotide sequence (SEQ ID NO: 7) | Aaggatgaaccacagagaagatccgcgcgtctttctgctaaacctgctcctccaaagccagagc ccaagcctaagaaagcccctgcaaagaaaggcggaggcggttcaggcggaggtggctctggc ggtggcggatcagtgagagaaagaggtcctcagagagtagcagctcacataactgggaccaga ggaagaagcaacacattgtcttctccaaactccaagaatgaaaaggctctgggccgcaaaataaa ctcctgggaatcatcaaggagtgggcattcattcctgagcaacttgcacttgaggaatggtgaactg gtcatccatgaaaaagggttttactacatctattcccaaacatactttcgatttcaggaggaaataaaa gaaaacacaaagaacgacaaacaaatggtccaatatatttacaaatacacaagttatcctgaccta tattgttgatgaaaagtgctagaaatagttgttggtctaaagatgcagaatatggactctattccatcta tcaaggggaatatttgagcttaaggaaaatgacagaattttttgtttctgtaacaaatgagcacttgat agacatggaccatgaagccagttttttcggggccttttagttggc |
| TRAIL-F3-C amino acid sequence (SEQ ID NO: 10) | VRERGPQRVAAHITGTRGRSNTLSSPNSKNEKALGRKINSWES SRSGHSFLSNLHLRNGELVIHEKGFYYIYSQTYFRFQEEIKENT KNDKQMVQYIYKYTSYPDPILLMKSARNSCWSKDAEYGLYSI YQGGIFELKENDRIFVSVTNEHLIDMDHEASFFGAFLVGGGGG SGGGGSGGGGSKDEPQRRSARLSAKPAPPKPEPKPKKAPAKK |

TABLE 1 -continued

The present invention relates to amino acid sequences
and nucleic acid sequences

| Name | Sequences |
|---|---|
| TRAIL-F3-C nucleotide sequence (SEQ ID NO: 9) | Gtgagagaaagaggtcctcagagagtagcagctcacataactgggaccagaggaagaagcaa<br>cacattgtcttctccaaactccaagaatgaaaaggctctgggccgcaaaataaactcctgggaatc<br>atcaaggagtgggcattcattcctgagcaacttgcacttgaggaatggtgaactggtcatccatgaa<br>aaagggttttactacatctattcccaaacatactttcgatttcaggaggaaataaaagaaaacacaaa<br>gaacgacaaacaaatggtccaatatatttacaaatacacaagttatcctgaccctatattgttgatgaa<br>aagtgctagaaatagttgttggtctaaagatgcagaatatggactctattccatctatcaaggggaa<br>tatttgagcttaaggaaaatgacagaattttttgtttctgtaacaaatgagcacttgatagacatggacc<br>atgaagccagttttttcggggccttttagttggcggtggaggcggttcaggcggaggtggctctgg<br>cggtggcggatcgaaggatgaaccacagagaagatccgcgcgtctttctgctaaacctgctcctc<br>caaagccagagcccaagcctaagaaagcccctgcaaagaaa |
| TRAIL-PC-N amino acid sequence | STVQEKQQNISPLGGGGSVRERGPQRVAAHITGTRGRSNTLSS<br>PNSKNEKALGRKINSWESSRSGHSFLSNLHLRNGELVIHEKGF<br>YYIYSQTYFRFQEEIKENTKNDKQMVQYIYKYTSYPDPILLMK<br>SARNSCWSKDAEYGLYSIYQGGIFELKENDRIFVSVTNEHLID<br>MDHEASFFGAFLVG |
| TRAIL-PC-N nucleotide sequence | agcactgttcaagagaaacaacagaatattagtccgctgGgtggaggcggttcagtgagagaaa<br>gaggtcctcagagagtagcagctcacataactgggaccagaggaagaagcaacacattgtcttct<br>ccaaactccaagaatgaaaaggctctgggccgcaaaataaactcctgggaatcatcaaggagtg<br>ggcattcattcctgagcaacttgcacttgaggaatggtgaactggtcatccatgaaaaagggttttac<br>tacatctattcccaaacatactttcgatttcaggaggaaataaaagaaaacacaaagaacgacaaac<br>aaatggtccaatatatttacaaatacacaagttatcctgaccctatattgttgatgaaaagtgctagaa<br>atagttgttggtctaaagatgcagaatatggactctattccatctatcaaggggaatatttgagctta<br>aggaaaatgacagaattttttgtttctgtaacaaatgagcacttgatagacatggaccatgaagccagt<br>tttttcggggccttttagttggc |

2) Construction of the Recombinant Expression Vector of TRAIL Variant Protein

In this example, pET21d and pQE30 were used as vectors for expression. For the convenience of cloning, Nco I and BamH I restriction endonuclease sites were respectively added to 5- or 3-end of genes encoding TRAIL, TRAIL-F3-N and TRAIL-F3-C. And the target genes obtained by enzyme digestion were cloned into the expression vector pET21d (purchased from Novagen) to construct expression plasmids pET21d-TRAIL, pET21d-TRAIL-F3-N and pET21d-TRAIL-F3-C, respectively. BamH I and Kpn I endonuclease sites were respectively added to 5- or 3-end of gene encoding TRAIL-PC-N. The target genes obtained by enzyme digestion were cloned into the expression vector pQE30 (purchased from Qiagen) to construct expression plasmids pQE30-TRAIL-PC-N. The construction methods of expression plasmids are all conventional methods described in Molecular Cloning, A Laboratory Manual (compiled and written by J. Sambrook, translated by Huang Peitang, published in 2008).

Figure 2:
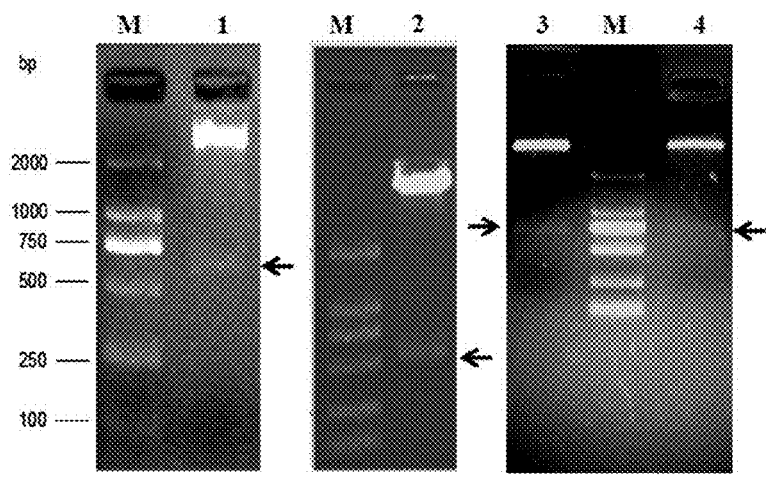
FIG. 2. Identification of the recombinant protein expression plasmids by dual-enzyme digestions. M: DNA molecular weight standards. 1: pET21d-TRAIL; 2: pQE30-TRAIL-PC-N; 3: pET21d-TRAIL-F3-N; 4: pET21d-TRAIL-F3-C. The arrows show the fragments of the target genes produced by enzyme digestion.

The constructed plasmids were analyzed by dual enzyme digestion (FIG. 2) followed by verification with DNA sequencing.

3) Construction and Screening of Recombinant Bacteria

The expression plasmids pET21d-TRAIL, pET21d-TRAIL-F3-N and pET21d-TRAIL-F3-C were transformed into E. coli BL21-DE3 according to the method described in Molecular Cloning, A Laboratory Manual (compiled and written by J. Sambrook, translated by Huang Peitang, published in 2008), and then positive clones were screened with LB plates containing ampicillin (100 μg/ml).

2. Induced Expression and Isolation and Purification of TRAIL Variant Proteins

Bacteria from different colonies were inoculated into a liquid LB medium containing ampicillin (100 μg/ml), and cultured at 37° C. with shaking until A600 nm=0.6-1. The expression plasmid pQE30-TRAIL-PC-N was transformed into E. coli M15 (purchased from Qiagen), and cultured in LB containing both ampicillin (100 μg/ml) and karamycin (30 μg/ml). To induce the expression of protein, 1 mM isopropyl-β-D-thiogalactopyranoside (IPTG) was added followed by incubation for additional 4-6 hours. The mixture was centrifuged for 10 min at 6,000 g, and the bacteria were collected and resuspended in lysis buffer (10 mM phosphate buffer, pH 7.6, 10% glycerol, 10 mM 2-mercaptoethanol). Phenylmethanesulfonyl fluoride (PMSF) was added into the solution to a final concentration of 1 mM. The bacteria were sonicated (power of 300-400 W, working for 10 s with an interval of 50 s) under ice bath conditions. After ultrasonication, the samples were centrifuged at 20,000 g for 15 min at 4° C. (this procedure was repeated four times). The supernatant was firstly loaded to a cation exchange SP-Sepharose column (purchased from GE Inc.) equilibrated with lysis buffer followed by wash with lysis buffer containing 0.2 M NaCl and elution with lysis buffer containing 0.8M NaCl. The eluted proteins were then loaded to Ni-NTA-Agarose (available from Qiagen Inc.) followed by elution with 50-300 mM imidazole. The endotoxins in the purified proteins were erased using the endotoxin removal kit (Genscript, Nanjing, China).

Figure 3:
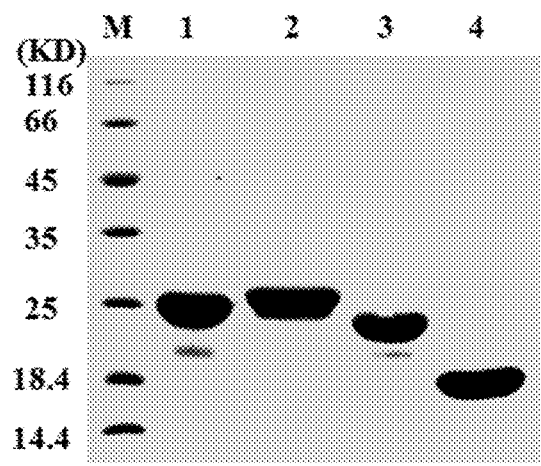
FIG. 3. SDS-PAGE eletrophoresis of the purified proteins. M: protein standards; 1: TRAIL-F3-C; 2: TRAIL-F3-N; 3: TRAIL-PC-N; 4: TRAIL.

As shown in FIG. 3, the molecular weights of proteins estimated by SDS-PAGE under reduced conditions were as follows: TRAIL, 17.8 KD; TRAIL-PC-N, 22.8 KD; TRAIL-F3-N, 26.3 KD; TRAIL-F3-C, 25.6 KD. The apparent molecular weights of all the proteins are consistent with their expected molecular weights.

These results demonstrated that the TRAIL and its variants TRAIL-F3-N, TRAIL-F3-C, and TRAIL-PC-N have been prepared.

The advantages of the present invention are explained below by way of experimental examples:

Experimental Example 1 Impact of Fusion Mode on the Activity of TRAIL Variants

1. Experimental Method

The in vitro cytotoxicity of the TRAIL variant proteins was determined according to the following methods.

The human liver cancer cell strain SMMC-7721 and human lung cancer cell strain A549 were cultured in RPMI 1640 containing 10% fetal bovine serum, 2 mM L-glutamine, 100 μg/ml streptomycin and 100 U/ml penicillin at 37° C. under 5% $CO_2$. $1 \times 10^4$ cells were inoculated onto 96-well plates. After cultured overnight, the medium was replaced with a 1640 medium containing 2% fetal bovine serum. Simultaneously, proteins at different concentrations were added into the cells. After treatment overnight, a CCK-8 solution was added and the A495 nm was measured using a microplate reader 2-4 h later. The survival rate of cells treated without protein was considered as 100%.

2. Experimental Results

Figure 4:
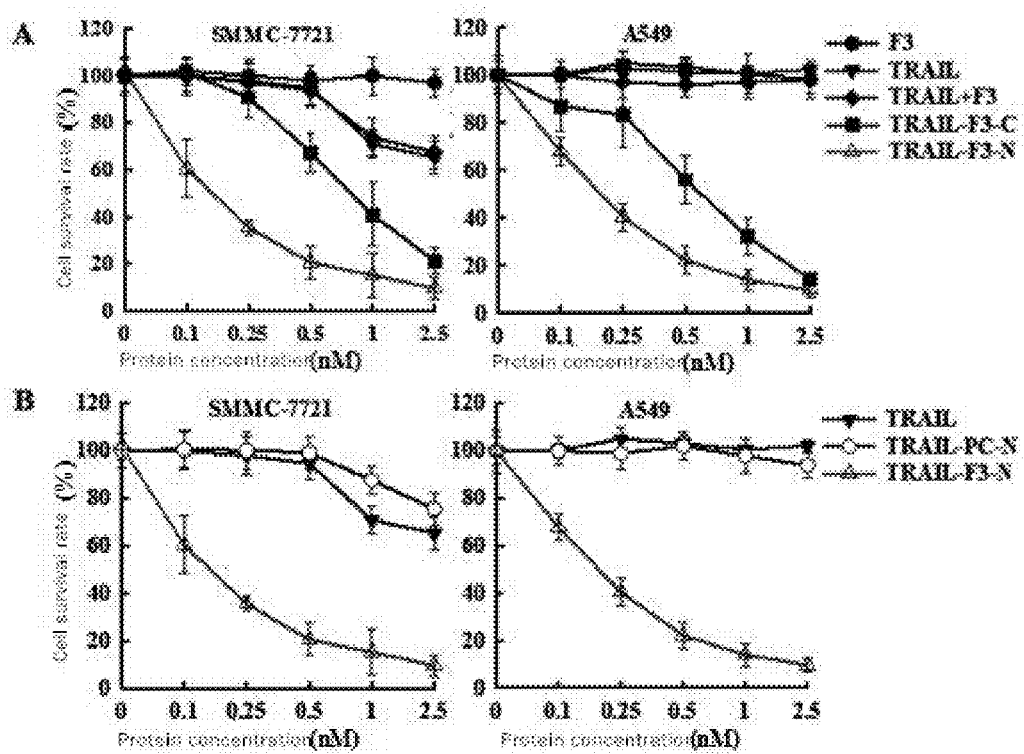
FIG. 4. Fusion to F3 enhances the cytotoxicity of TRAIL in tumor cells.

The results were shown in FIG. 4.

1. The cytotoxicity of TRAIL-F3-N and TRAIL-F3-C in both liver cancer cell SMMC-7721 and lung cancer cell A549 increased along the increase of the protein concentration (FIG. 4A), demonstrating that these TRAIL variants declared in the present invention are cytotoxic to tumor cells.

2. However, the unconjugated F3 peptide has no obvious cytotoxicity in liver cancer cell SMMC-7721 and lung cancer cell A549 cells under the same conditions. Unconjugated TRAIL showed cytotoxicity in these tumor cells at high concentrations. Mixture of F3 peptide and TRAIL is similar to TRAIL in terms of cytotoxicity, indicating that combination with F3 did not increase the TRAIL activity. However, the cytotoxicity of TRAIL-F3-N and TRAIL-F3-C produced by fusing F3 to the N-terminus or C-terminus of TRAIL respectively was higher than that of TRAIL at the same concentration. (FIG. 4A) The results demonstrated that the cytotoxicity of TRAIL could not be enhanced by mixing of TRAIL to F3 peptide.

3. With respect to the same tumor cell, TRAIL-F3-N has a more potent cytotoxicity than TRAIL-F3-C (FIG. 4B), indicating that the F3 fused at the N-terminus of TRAIL is more efficient than F3 fused at the C-terminus to enhance the cytotoxicity of TRAIL.

4. The variant TRAIL-PC-N produced by fusing a random control PC peptide at the N-terminus of TRAIL was not significantly different from TRAIL in terms of tumor cytotoxicity (FIG. 4B), indicating that only fused F3 peptide can enhance the anti-tumor activity of TRAIL.

The experimental results show that, of above three variant proteins, the cytotoxicity of TRAIL-F3-N and TRAIL-F3-C of the present invention in tumor cells are significantly higher than that of TRAIL. However, TRAIL-PC-N does not differ from TRAIL in cytotoxicity in tumor cells. Especially, TRAIL-F3-N has the strongest cytotoxicity.

Experimental Example 2 Detection of Selectivity of Variant Proteins for Tumor Cells 1. Experimental Method To determine the selectivity, the cytotoxicity of TRAIL variant proteins in tumor cells and normal cells was compared. $1 \times 10^4$ cells (100 μl) were inoculated onto 96-well plates. After being cultured overnight, proteins dissolved in 1640 medium supplemented with 2% fetal bovine serum were added into the cells. After treatment overnight, 10 μl CCK-8 was added followed by measuring A495 nm using a microplate reader 2-4 h later. The survival rate of cells treated without proteins was considered as 100%.

2. Experimental Results

The results were shown in FIG. 5.

1. Cytotoxicity in tumor cells: TRAIL-F3-N and TRAIL-F3-C showed cytotoxicity in liver cancer (SMMC-7721, SK-HEP-1, QGY-7703, QGY-7701, BEL-7402, BEL-7404, PLC/PRF/5), lung cancer (A549, SPC-A1, NCI-H358, NCI-H1650, 95D, NCI-H446, NCI-H1299), colon cancer (COLO 205, SW480), breast cancer (MDA-MB-231, MDA-MB-435S) and glioma (T98G) cells, which was obviously stronger than that of TRAIL. The IC50s of TRAIL-F3-N for these cells were ranged from 0.1 to 0.5 nM, which was 10-40 times lower than the IC50s of TRAIL.

2. Cytotoxicity in normal cells: as same as TRAIL, TRAIL-F3-N and TRAIL-F3-C showed no obvious cytotoxicity in normal cells (such as skin fibroblasts HSF and COS-7).

These results demonstrated that the TRAIL variant proteins, including TRAIL-F3-N and TRAIL-F3-C prepared in the present invention, exhibited stronger cytotoxicity but preserved the selectivity of TRAIL.

Experimental Example 3 Affinity of TRAIL Variant Protein TRAIL-F3-N for Tumor Cells 1. Experimental Method The F3 peptides, TRAIL, and TRAIL-F3-N were labelled with FITC followed by incubation with cells. The binding of peptide or proteins to the cells were determined using flow cytometry. To label with FITC, the pH of peptide/protein solution was adjusted to 8.5 with $Na_2CO_3$. Subsequently, FITC was added into the solution at a molar ratio of peptide/protein to dye of 1:24 followed by incubation at 25° C. for 1 h in darkness. Unconjugated FITC were removed by dialyzing. Approximately, $2 \times 10^5$ cells were resuspended in 500 μl of a phosphate buffer (PBS, 50 mM, 150 mM NaCl, pH 7.4). Different concentrations of FITC-labeled peptide/protein was added into the cells and incubated at 4° C. for 1 h. The cells were washed with PBS twice followed by flow cytometry.

2. Experimental Results

The results were shown in FIG. 6.

1. As shown in FIG. 6A, flow cytometry analysis demonstrated that the positive rate of SMMC-7721 cells incubated with unconjugated F3 peptide (4 μM) was 55%, indicating that F3 could bind to tumor cells. The binding rates of unconjugated TRAIL to SMMC-7721 at concentrations of 2.5, 5.0 and 7.5 nM were 5.8%, 13.2% and 25.8%, respectively. However, the binding rates of TRAIL-F3-N at 2.5, 5.0 and 7.5 nM to SMMC-7721 were 42%, 63.1% and 88.8%, indicating that the binding ability of TRAIL-F3-N to tumor cells was higher than that of the unconjugated F3 peptide and TRAIL protein.

That is to say, at lower doses, the affinity of the variant proteins of the present invention for tumor cells is higher than that of the unconjugated F3 and TRAIL at high doses, indicating that F3 and TRAIL fused in a particular manner as in the present invention can exert synergetic effects in cell binding 2. When the same dose of F3 peptides (4 μM) were incubated with different types of tumor cells and normal cells, the binding rate of F3 peptides to tumor cells (50%-90%) was higher than that to normal cells (<30%) (FIG. 6B). Similarly, when 1, 2.5 and 5 nM TRAIL and TRAIL-F3-N was incubated with a variety of tumor cells and normal cells, flow cytometry analysis demonstrated that TRAIL-F3-N binds to tumor cells more strongly than TRAIL at the same dose. But the normal cells-binding of TRAIL-F3-N is similar to that of TRAIL (FIG. 6C).

These results indicated that the affinity of the TRAIL variant protein TRAIL-F3-N for normal cells is similar to that of TRAIL, but the affinity of TRAIL-F3-N for tumor cells is higher than that of TRAIL. At a certain concentration, TRAIL-F3-N can effectively bind to tumor cells without binding to normal cells.

Meanwhile, at the same dose, the affinity of the variant protein of the present invention for tumor cells was higher than that of unconjugated F3 and TRAIL, indicating that F3 and TRAIL fused in a particular manner can exert synergetic effects in cell binding.

Experimental Example 4 TRAIL Variant Protein TRAIL-F3-N Induces Tumor Cell Apoptosis 1. Experimental Method Tumor cells were treated with proteins and stained with Annexin V (green fluorescence) in combination with Propidium Iodide (PI, red fluorescence). The apoptotic cells were detected by fluorescence microscope observation or flow cytometry. Annexin V+PI− cells were considered as apoptotic cells. Annexin V+PI+ cells were considered as necrotic cells. And Annexin V−PI− cells were cells were considered as living cells.

2. Experimental Results

After treatment with 2 nM TRAIL-F3-N for 4 h, liver cancer cells SMMC-7721 were stained with Annexin V/PI and observed using a fluorescence microscope. It was found that most cells were apoptotic cells (Annexin V+PI−) (FIG. 7A). Flow cytometry demonstrated that the percentage of apoptotic cells treated with 1, 2, or 5 nM TRAIL-F3-N was 48.6%, 74.4% and 85.9%, respectively, compared to 0.19%, 0.22% and 0.4% of corresponding necrotic cells (FIG. 7B). DAPI staining was used to visualize changes in nuclei. It was found that nuclear condensation was observed in a large number of cells treated with TRAIL-F3-N for 8 h. After treatment for 24 h, debris was observed in numerous (FIG. 7C). TUNEL staining combined with flow cytometry analysis showed that the TUNEL positive rate of cells treated with TRAIL-F3-N was 66.3%, which further confirmed the DNA fragmentation (FIG. 7D). To investigate the involvement of caspase, the cells were pre-incubated with Pan-caspase inhibitor Z-VAD-FMK for 2 h prior to treatment with protein. The caspase inhibitor was found to significantly inhibit the cytotoxicity TRAIL-F3-N in tumor cells. And the activities of caspase 3, 8 and 9 were detectable, indicating that these enzymes were activated in cells treated with TRAIL-F3-N. Compared to TRAIL, TRAIL-F3-N activated more caspases (FIG. 7E).

These results showed that the TRAIL variant TRAIL-F3-N declared in the present invention induces Caspase-dependent tumor cell apoptosis. Furthermore, the apoptosis-inducing ability of TRAIL-F3-N was higher than that of TRAIL.

Experimental Example 5 In Vitro Stability of the TRAIL Variant Protein TRAIL-F3-N 1. Experimental Method Plasma or whole blood was mixed with the same volume of protein. After incubation at 37° C. for different times, the cytotoxicity of the protein was measured. Reduction of activity reveals the in vitro stability of protein.

2. Experimental Results

The results were shown in FIG. 8.

The activity of TRAIL in plasma decreased along incubation time. The activity of TRAIL was reduced by at least half after incubation for 3 h. Most proteins lost activity after incubation for 24 h. However, TRAIL-F3-N was stable in plasma, and the activity of TRAIL-F3-N was not significantly decreased even incubated for 72 h (FIG. 8A).

The results of FIG. 8B showed that TRAIL-F3-N was also stable in whole blood. No obvious decrease in activity was observed after incubated for 6 h.

These results demonstrate that the TRAIL variant protein TRAIL-F3-N of the present invention is more stable than TRAIL. In other words, fusion of F3 to TRAIL follow the way described in the present invention can effectively improve the stability of TRAIL in vitro and facilitate storage.

Experimental Example 6 In Vivo Tumor-targeting of the TRAIL Variant Protein TRAIL-F3-N 1. Experimental Method Nude mice were inoculated subcutaneously with COLO 205 ($5 \times 10^5$/mouse) to establish a tumor-bearing model. Meanwhile, TRAIL-F3-N and TRAIL proteins were labeled with a fluorescent dye CF750 according to a conventional method. Tail vein administration was performed when the tumor grew to 50-100 mm³, Then, the tumor uptake was dynamically detected using optical imaging system. At the end of the observation, the tumor-bearing nude mice were sacrificed, the vital organs and tissues were removed, and the distribution of the protein in different organs and tissues was detected by an optical imaging system.

2. Experimental Results

The optical images were showed in FIGS. 9A and 9B. After administration for 10 h, TRAIL-F3-N was observed to accumulate at the tumor site. The accumulation of proteins in the tumor gradually increased to its peak at about 48 h. Tumors uptake of TRAIL was observed at the tumor site 6 h post administration was quicker than that of TRAIL-F3-N, which can be. However, the tumor uptake of TRAIL was obviously less than that of TRAIL-F3-N, indicating fusion to F3 increased the tumor uptake of TRAIL.

The animals were sacrificed at 72 h post injection and the tissue distribution of the protein was shown in FIGS. 9C and 9D. TRAIL and TRAIL-F3-N were predominantly distributed in kidney, liver and tumor tissues. Since protein was eliminated by liver and kidney, rich proteins were detected in liver and kidney of mice injected with TRAIL and TRAIL-F3-N. However, the protein content in the tumor tissue was significantly higher than that in tissues other than the liver and kidney, indicating that both TRAIL-F3-N and TRAIL proteins were tumor-homing. However, the tumor-targeting of TRAIL-F3-N was greater than that of TRAIL. In other words, fusion of F3 to TRAIL in the way described in the present invention can effectively improve the tumor targeting property of TRAIL.

Experimental Example 7 In Vivo Anti-Tumor Effect of TRAIL Variant Protein TRAIL-F3-N Against TRAIL-Sensitive Cells 1. Experimental Method An in vitro cytotoxicity assay showed that colon cancer COLO 205 cells were TRAIL-sensitive. Nude mice were inoculated subcutaneously with COLO 205 ($5 \times 10^5$/mouse). TRAIL and TRAIL-F3-N proteins (0.1 mg/kg and 0.3 mg/kg) were intratumorally injected once a day for 3 consecutive days when the tumor grew to 100-200 mm³. An equal volume of PBS was used as a control. The tumor size was measured periodically.

In order to further test the anti-tumor effects of proteins via tail vein injection, a single dose (10 mg/kg) of TRAIL and TRAIL-F3-N proteins were injected via the tail vein at 6 days after subcutaneous inoculation with COLO 205 cells.

2. Experimental Results

The anti-tumor effect of intratumorally injected proteins was shown in FIG. 10A. It was found that the tumor in mice treated with TRAIL or TRAIL-F3-N protein grew slower than that in mice of control group, indicating that both proteins are tumor suppressive. Definitely, the anti-tumor effect of TRAIL-F3-N was better than that of TRAIL. The tumors in mice treated with TRAIL-F3-N were smaller than that in mice treated with the same dose of TRAIL. Moreover, the anti-tumor effect of 0.1 mg/kg TRAIL-F3-N was better than that of 0.3 mg/kg TRAIL.

The anti-tumor effect of intravenously injected proteins was shown in FIG. 10B. Both TRAIL and TRAIL-F3-N can significantly inhibit tumor growth. The tumors in mice treated with TRAIL-F3-N were smaller than the tumors in mice treated with TRAIL at same dose, indicating that the anti-tumor effect of TRAIL-F3-N was better than that of TRAIL. Moreover, a single dose of TRAIL-F3-N at different amount was intravenously injected in mice bearing tumor grafts. The results are shown in FIG. 10C. Compared with the control group, the tumor growth was suppressed in all protein-treated groups. Tumor growth suppression increased along the increase of amount of protein. At the end of the experiment the tumors in mice treated with TRAIL-F3-N at 5 and 10 mg/kg were significantly smaller than that in the control group (FIG. 10D).

These results demonstrated that the TRAIL variant protein TRAIL-F3-N of the present invention showed greater in vivo anti-tumor effect than TRAIL. In other words, fusion of F3 to TRAIL in the way of the present invention can effectively improve the in vivo anti-tumor effect of TRAIL.

Experimental Example 8 In Vivo Anti-Tumor Activity of TRAIL Variant Protein TRAIL-F3-N Against TRAIL-Resistant Cells 1. Experimental Method An in vitro cytotoxicity assay showed that lung cancer cells A549 were TRAIL-resistant cells. Nude mice were inoculated subcutaneously with A549 ($5 \times 10^6$/mouse). TRAIL and TRAIL-F3-N proteins at different doses (1 mg/kg and 3 mg/kg) were intratumorally injected into the mice once a day, for 3 consecutive days in total when the tumor grew to approximately 50 mm$^3$ on average. An equal volume of PBS was used as a control.

In addition, TRAIL (10 mg/kg) and TRAIL-F3-N (5, 10, and 20 mg/kg) were intravenously injected into the mice bearing tumor grafts for 5 days. The same volume of PBS was injected into the mice of control group.

2. Experimental Results

Anti-tumor effect of the intratumorally injected proteins was shown in FIG. 11A. It was found that only 3 mg/kg TRAIL suppressed the tumor growth. But the tumor size in TRAIL group was not significantly different from that in the control group at the same time points. However, TRAIL-F3-N was more potent than TRAIL in A549 growth suppression. The tumor sizes of mice treated with 1 mg/kg and 3 mg/kg TRAIL-F3-N were significantly smaller than that of mice in the control groups.

The anti-tumor effect of the intravenously injected proteins was shown in FIG. 11B. The tumor sizes of mice treated with 10 mg/kg TRAIL were similar to that of mice in the control group. However, the tumor growth in mice treated with 5 mg/kg TRAIL-F3-N was significantly slower than that in mice in the control group. Compared to 5 mg/kg, 10 and 20 mg/kg TRAIL-F3-N showed greater tumor suppression. At the end of the experiment, the average tumor size and average tumor weight of mice treated with 10 mg/kg TRAIL were not significantly different from those in the control group. However, the average tumor size and average tumor weight of mice treated with 10 or 20 mg/kg TRAIL-F3-N were significantly lower than those in the control group. Especially, the average tumor weight of 10 mg/kg TRAIL-F3-N-treated mice was significantly lighter than that of the same dose of TRAIL-treated mice (FIG. 11C).

These results demonstrated that the TRAIL variant protein TRAIL-F3-N of the present invention has an obvious anti-tumor effect on TRAIL-resistant tumors. TRAIL-F3-N could be used for the treatment of TRAIL-resistant tumors, and achieved completely unpredicted technical effects.

Experimental Example 9 Short-Term Acute Toxicity of TRAIL Variant Protein TRAIL-F3-N 1. Experimental Method BALB/c mice (SPF grade) were injected with 20 mg/kg of TRAIL-F3-N, TRAIL or an equal volume of PBS via the tail vein every other day, for 10 days in total. The body weights of the mice were measured periodically. The average body weight of mice at day 0 was considered as 100%.

2. Experimental Results

As shown in FIG. 12A, the average body weight of the mice was gradually increased after administration. The difference between different groups in average body weight was not significant. Three days after the last administration, the mice were sacrificed for liver and kidney histochemistry examination and function analysis. As shown in FIG. 12B, the levels of glutamic-pyruvic transaminase (ALT) and glutamic oxalacetic transaminase (AST) of mice in three groups were similar. The average urea nitrogen (UREAL) of TRAIL-F3-N-treated mice was 1.6 times higher than that of PBS group. But the uric acid (UA) of TRAIL-F3-N-treated mice was about 0.7 times of that of PBS group. In addition, no obvious abnormality in structure was observed in liver and kidney from mice injected with TRAIL-F3-N or TRAIL (FIG. 12C). These results demonstrated that TRAIL-F3-N has no obvious acute liver and renal toxicity.

The purified TRAIL variant proteins TRAIL-F3-N and TRAIL-F3-C of the present invention have been prepared by means of genetic engineering, and obviously have a higher cytotoxicity in tumor cells than TRAIL. Of these variants, TRAIL-F3-N is superior to TRAIL in terms of tumor cell affinity, stability, ability to induce tumor cell apoptosis, tumor-targeting property and in vivo anti-tumor effects. Especially, the TRAIL variant protein TRAIL-F3-N has a good therapeutic effect on TRAIL-resistant tumors and can be used to treat TRAIL-resistant tumors.

In summary, the TRAIL variant proteins TRAIL-F3-N and TRAIL-F3-C of the present invention have excellent properties and have promising prospects in clinical application.

The invention claimed is:

1. A tumor necrosis factor-related apoptosis-inducing ligand variant, characterized in that the variant is a fusion protein of a tumor necrosis factor-related apoptosis-inducing ligand and an F3 peptide, and the F3 peptide is fused to the N-terminus or C-terminus of the tumor necrosis factor-related apoptosis-inducing ligand by a linker.

2. The tumor necrosis factor-related apoptosis-inducing ligand variant according to claim 1, characterized in that the amino acid sequence of said tumor necrosis factor-related apoptosis-inducing ligand is as shown in SEQ ID NO: 2.

3. The tumor necrosis factor-related apoptosis-inducing ligand variant according to claim 1, characterized in that the amino acid sequence of said F3 peptide is as shown in SEQ ID NO: 4.

4. The tumor necrosis factor-related apoptosis-inducing ligand variant according to claim 3, characterized in that said F3 peptide is encoded by the nucleotide sequence as shown in SEQ ID NO: 3.

5. The tumor necrosis factor-related apoptosis-inducing ligand variant according to claim 1, characterized in that said linker consists of 2-20 amino acids.

6. The tumor necrosis factor-related apoptosis-inducing ligand variant according to claim 5, characterized in that said linker is a (G4S)3 linker and the amino acid sequence thereof is as shown in SEQ ID NO: 6.

7. The tumor necrosis factor-related apoptosis-inducing ligand variant according to claim 1, encoded by the nucleotide sequence as shown in SEQ ID NO: 7 or 9.

8. The tumor necrosis factor-related apoptosis-inducing ligand variant according to claim 6, characterized in that the amino acid sequence thereof is as shown in SEQ ID NO: 8 or 10.

9. A nucleotide sequence, comprising a coding sequence of a tumor necrosis factor-related apoptosis-inducing ligand and a coding sequence of an F3 peptide which are linked by a coding sequence of a linker.

10. The nucleotide sequence according to claim 9, characterized in that the coding sequence of said tumor necrosis factor-related apoptosis-inducing ligand is as shown in SEQ ID NO: 1.

11. The nucleotide sequence according to claim 9, characterized in that the coding sequence of said F3peptide is as shown in SEQ ID NO: 3.

12. The nucleotide sequence according to claim 9, characterized in that said linker is a (G4S)3 linker, and the nucleotide sequence thereof is as shown in SEQ ID NO: 5.

13. The nucleotide sequence according to claim 9, characterized in being as shown in SEQ ID NO: 7 or 9.

14. A recombinant vector or a recombinant bacterium comprising the nucleotide sequence according to claim 9.

15. A method for preparing the tumor necrosis factor-related apoptosis-inducing ligand variant according to claim 1, comprising preparing a nucleotide sequence comprising a coding sequence of a tumor necrosis factor-related apoptosis-inducing ligand and a coding sequence of an F3 peptide which are linked by a coding sequence of a linker.

16. A method for preparing a drug composition, comprising mixing the tumor necrosis factor related apoptosis inducing ligand variant according to claim 1 and a pharmaceutically acceptable adjuvant, wherein the drug composition is effective in treating a cell proliferative disease.

17. The method according to claim 16, characterized in that said cell proliferative disease is a tumor or an autoimmune disease.

18. An anti-tumor drug, comprising the tumor necrosis factor-related apoptosis-inducing ligand variant according to claim 1 as an active ingredient and a pharmaceutically acceptable adjuvant.

* * * * *

SEQUENCE LISTING

<160> NUMBER OF SEQ ID NOS: 15

<210> SEQ ID NO 1
<211> LENGTH: 504
<212> TYPE: DNA
<213> ORGANISM: Artificial Sequence
<220> FEATURE:
<223> OTHER INFORMATION: TRAIL114-281 nucleic acid sequence

<400> SEQUENCE: 1

```
gtgagagaaa gaggtcctca gagagtagca gctcacataa ctgggaccag aggaagaagc    60
aacacattgt cttctccaaa ctccaagaat gaaaaggctc tgggccgcaa aataaactcc   120
tgggaatcat caaggagtgg gcattcattc ctgagcaact tgcacttgag gaatggtgaa   180
ctggtcatcc atgaaaaagg ttttactac atctattccc aaacatactt tcgatttcag    240
gaggaaataa agaaaacac aaagaacgac aaacaaatgg tccaatatat ttacaaatac    300
acaagttatc ctgaccctat attgttgatg aaaagtgcta aaatagttg ttggtctaaa    360
gatgcagaat atggactcta ttccatctat caagggggaa tatttgagct taaggaaaat   420
gacagaattt ttgtttctgt aacaaatgag cacttgatag acatggacca tgaagccagt   480
tttttcgggg cctttttagt tggc                                          504
```

<210> SEQ ID NO 2
<211> LENGTH: 168
<212> TYPE: PRT
<213> ORGANISM: Artificial Sequence
<220> FEATURE:
<223> OTHER INFORMATION: TRAIL114-281 amino acid sequence

<400> SEQUENCE: 2

```
Val Arg Glu Arg Gly Pro Gln Arg Val Ala Ala His Ile Thr Gly Thr
  1               5                  10                  15

Arg Gly Arg Ser Asn Thr Leu Ser Ser Pro Asn Ser Lys Asn Glu Lys
            20                  25                  30

Ala Leu Gly Arg Lys Ile Asn Ser Trp Glu Ser Ser Arg Ser Gly His
        35                  40                  45

Ser Phe Leu Ser Asn Leu His Leu Arg Asn Gly Glu Leu Val Ile His
    50                  55                  60

Glu Lys Gly Phe Tyr Tyr Ile Tyr Ser Gln Thr Tyr Phe Arg Phe Gln
 65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
            100                 105                 110

Ala Arg Asn Ser Cys Trp Ser Lys Asp Ala Glu Tyr Gly Leu Tyr Ser
        115                 120                 125

Ile Tyr Gln Gly Gly Ile Phe Glu Leu Lys Glu Asn Asp Arg Ile Phe
    130                 135                 140

Val Ser Val Thr Asn Glu His Leu Ile Asp Met Asp His Glu Ala Ser
145                 150                 155                 160

Phe Phe Gly Ala Phe Leu Val Gly
                165
```

<210> SEQ ID NO 3
<211> LENGTH: 93
<212> TYPE: DNA
<213> ORGANISM: Artificial Sequence
<220> FEATURE:
<223> OTHER INFORMATION: F3 nucleic acid sequence

<400> SEQUENCE: 3

```
aaggatgaac cacagagaag atccgcgcgt ctttctgcta aacctgctcc tccaaagcca    60
gagcccaagc ctaagaaagc ccctgcaaag aaa                                 93
```

<210> SEQ ID NO 4
<211> LENGTH: 31
<212> TYPE: PRT
<213> ORGANISM: Artificial Sequence
<220> FEATURE:
<223> OTHER INFORMATION: F3 peptide sequence

<400> SEQUENCE: 4

Lys Asp Glu Pro Gln Arg Arg Ser Ala Arg Leu Ser Ala Lys Pro Ala
1               5                   10                  15

Pro Pro Lys Pro Glu Pro Lys Pro Lys Ala Pro Ala Lys Lys
            20                  25                  30

<210> SEQ ID NO 5
<211> LENGTH: 45
<212> TYPE: DNA
<213> ORGANISM: Artificial Sequence
<220> FEATURE:
<223> OTHER INFORMATION: G4S nucleic acid sequence

<400> SEQUENCE: 5
ggtggaggcg gttcaggcgg aggtggctct ggcggtggcg gatcg          45

<210> SEQ ID NO 6
<211> LENGTH: 15
<212> TYPE: PRT
<213> ORGANISM: Artificial Sequence
<220> FEATURE:
<223> OTHER INFORMATION: G4S linker

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 642
<212> TYPE: DNA
<213> ORGANISM: Artificial Sequence
<220> FEATURE:
<223> OTHER INFORMATION: TRAIL-F3-N nucleotide sequence

<400> SEQUENCE: 7
aaggatgaac cacagagaag atccgcgcgt ctttctgcta aacctgctcc tccaaagcca     60
gagcccaagc ctaagaaagc ccctgcaaag aaaggcggag gcggttcagg cggaggtggc    120
tctggcggtg gcggatcagt gagagaaaga ggtcctcaga gagtagcagc tcacataact    180
gggaccagag aagaagcaa cacattgtct ctctccaaact ccaagaatga aaaggctctg    240
ggccgcaaaa taaactcctg ggaatcatca aggagtgggc attcattcct gagcaacttg    300
cacttgagga atggtgaact ggtcatccat gaaaagggt tttactacat ctattcccaa    360
acatactttc gatttcagga ggaaataaaa gaaaacacaa agaacgacaa acaaatggtc    420
caatatattt acaaatacac aagttatcct gaccctatat tgttgatgaa agtgctaga    480 aatagttgtt ggtctaaaga tgcagaatat ggactctatt ccatctatca aggggaata    540 tttgagctta aggaaaatga cagaattttt gtttctgtaa caaatgagca cttgatagac    600
atggaccatg aagccagttt tttcggggcc tttttagttg gc                       642

<210> SEQ ID NO 8
<211> LENGTH: 214
<212> TYPE: PRT
<213> ORGANISM: Artificial Sequence
<220> FEATURE:
<223> OTHER INFORMATION: TRAIL-F3-N amino acid sequence

<400> SEQUENCE: 8

```
Lys Asp Glu Pro Gln Arg Arg Ser Ala Arg Leu Ser Ala Lys Pro Ala
1               5                   10                  15

Pro Pro Lys Pro Glu Pro Lys Pro Lys Ala Pro Ala Lys Lys Gly
            20                  25                  30

Gly Gly Gly Ser Gly Gly Gly Ser Gly Gly Gly Ser Val Arg
        35                  40                  45

Glu Arg Gly Pro Gln Arg Val Ala Ala His Ile Thr Gly Thr Arg Gly
50                  55                  60

Arg Ser Asn Thr Leu Ser Ser Pro Asn Ser Lys Asn Glu Lys Ala Leu
65                  70                  75                  80

Gly Arg Lys Ile Asn Ser Trp Glu Ser Ser Arg Ser Gly His Ser Phe
                85                  90                  95

Leu Ser Asn Leu His Leu Arg Asn Gly Glu Leu Val Ile His Glu Lys
            100                 105                 110

Gly Phe Tyr Tyr Ile Tyr Ser Gln Thr Tyr Phe Arg Phe Gln Glu Glu
        115                 120                 125

Ile Lys Glu Asn Thr Lys Asn Asp Lys Gln Met Val Gln Tyr Ile Tyr
130                 135                 140

Lys Tyr Thr Ser Tyr Pro Asp Pro Ile Leu Leu Met Lys Ser Ala Arg
145                 150                 155                 160

Asn Ser Cys Trp Ser Lys Asp Ala Glu Tyr Gly Leu Tyr Ser Ile Tyr
                165                 170                 175

Gln Gly Gly Ile Phe Glu Leu Lys Glu Asn Asp Arg Ile Phe Val Ser
            180                 185                 190

Val Thr Asn Glu His Leu Ile Asp Met Asp His Glu Ala Ser Phe Phe
            195                 200                 205

Gly Ala Phe Leu Val Gly
        210
```

<210> SEQ ID NO 9
<211> LENGTH: 642
<212> TYPE: DNA
<213> ORGANISM: Artificial Sequence
<220> FEATURE:
<223> OTHER INFORMATION: TRAIL-F3-C nucleotide sequence

<400> SEQUENCE: 9

```
gtgagagaaa gaggtcctca gagagtagca gctcacataa ctgggaccag aggaagaagc      60
aacacattgt cttctccaaa ctccaagaat gaaaaggctc tgggccgcaa aataaactcc     120
tgggaatcat caaggagtgg gcattcattc ctgagcaact gcacttgag gaatggtgaa      180
ctggtcatcc atgaaaaagg gttttactac atctattccc aaacatactt tcgatttcag     240
gaggaaataa agaaaacac aaagaacgac aaacaaatgg tccaatatat ttacaaatac      300
acaagttatc ctgaccctat attgttgatg aaaagtgcta gaaatagttg ttggtctaaa     360
gatgcagaat atggactcta ttccatctat caaggggaa tatttgagct taaggaaaat      420
gacagaattt ttgtttctgt aacaaatgag cacttgatag acatggacca tgaagccagt     480
ttttcgggg cctttttagt tggcggtgga ggcggttcag gcggaggtgg ctctggcggt      540
ggcggatcga aggatgaacc acagagaaga tccgcgcgtc tttctgctaa acctgctcct     600
ccaaagccag agcccaagcc taagaaagcc cctgcaaaga aa                         642
```

<210> SEQ ID NO 10
<211> LENGTH: 214
<212> TYPE: PRT
<213> ORGANISM: Artificial Sequence
<220> FEATURE:
<223> OTHER INFORMATION: TRAIL-F3-C amino acid sequence

<400> SEQUENCE: 10

Val Arg Glu Arg Gly Pro Gln Arg Val Ala Ala His Ile Thr Gly Thr
1               5                   10                  15

Arg Gly Arg Ser Asn Thr Leu Ser Ser Pro Asn Ser Lys Asn Glu Lys
            20                  25                  30

Ala Leu Gly Arg Lys Ile Asn Ser Trp Glu Ser Ser Arg Ser Gly His
        35                  40                  45

Ser Phe Leu Ser Asn Leu His Leu Arg Asn Gly Glu Leu Val Ile His
    50                  55                  60

Glu Lys Gly Phe Tyr Tyr Ile Tyr Ser Gln Thr Tyr Phe Arg Phe Gln
65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
            100                 105                 110

Ala Arg Asn Ser Cys Trp Ser Lys Asp Ala Glu Tyr Gly Leu Tyr Ser
        115                 120                 125

Ile Tyr Gln Gly Gly Ile Phe Glu Leu Lys Glu Asn Asp Arg Ile Phe
    130                 135                 140

Val Ser Val Thr Asn Glu His Leu Ile Asp Met Asp His Glu Ala Ser
145                 150                 155                 160

Phe Phe Gly Ala Phe Leu Val Gly Gly Gly Gly Ser Gly Gly Gly
                165                 170                 175

Gly Ser Gly Gly Gly Gly Ser Lys Asp Glu Pro Gln Arg Arg Ser Ala
            180                 185                 190

Arg Leu Ser Ala Lys Pro Ala Pro Pro Lys Pro Glu Pro Lys Pro Lys
        195                 200                 205

Lys Ala Pro Ala Lys Lys
    210

<210> SEQ ID NO 11
<211> LENGTH: 39
<212> TYPE: DNA
<213> ORGANISM: Artificial Sequence
<220> FEATURE:
<223> OTHER INFORMATION: Nucleic acid sequence of PC peptide

<400> SEQUENCE: 11
agcactgttc aagagaaaca acagaatatt agtccgctg                          39

<210> SEQ ID NO 12
<211> LENGTH: 13
<212> TYPE: PRT
<213> ORGANISM: Artificial Sequence
<220> FEATURE:
<223> OTHER INFORMATION: PC peptide sequence

<400> SEQUENCE: 12

Ser Thr Val Gln Glu Lys Gln Gln Asn Ile Ser Pro Leu
1               5                   10

<210> SEQ ID NO 13

<211> LENGTH: 558
<212> TYPE: DNA
<213> ORGANISM: Artificial Sequence
<220> FEATURE:
<223> OTHER INFORMATION: TRAIL-PC-N nucleotide sequence

<400> SEQUENCE: 13

```
agcactgttc aagagaaaca acagaatatt agtccgctgg gtggaggcgg ttcagtgaga      60
gaaagaggtc ctcagagagt agcagctcac ataactggga ccagaggaag aagcaacaca     120
ttgtcttctc caaactccaa gaatgaaaag gctctgggcc gcaaaataaa ctcctgggaa     180
tcatcaagga gtgggcattc attcctgagc aacttgcact tgaggaatgg tgaactggtc     240
atccatgaaa aagggtttta ctacatctat tcccaaacat actttcgatt tcaggaggaa     300
ataaaagaaa acacaaagaa cgacaaacaa atggtccaat atatttacaa atacacaagt     360
tatcctgacc ctatattgtt gatgaaaagt gctagaaata gttgttggtc taaagatgca     420
gaatatggac tctattccat ctatcaaggg ggaatatttg agcttaagga aaatgacaga     480
atttttgttt ctgtaacaaa tgagcacttg atagacatgg accatgaagc cagttttttc     540
ggggcctttt tagttggc                                                    558
```

<210> SEQ ID NO 14
<211> LENGTH: 186
<212> TYPE: PRT
<213> ORGANISM: Artificial Sequence
<220> FEATURE:
<223> OTHER INFORMATION: TRAIL-PC-N amino acid sequence

<400> SEQUENCE: 14

```
Ser Thr Val Gln Glu Lys Gln Gln Asn Ile Ser Pro Leu Gly Gly Gly
  1               5                  10                  15

Gly Ser Val Arg Glu Arg Gly Pro Gln Arg Val Ala Ala His Ile Thr
             20                  25                  30

Gly Thr Arg Gly Arg Ser Asn Thr Leu Ser Ser Pro Asn Ser Lys Asn
         35                  40                  45

Glu Lys Ala Leu Gly Arg Lys Ile Asn Ser Trp Glu Ser Ser Arg Ser
     50                  55                  60

Gly His Ser Phe Leu Ser Asn Leu His Leu Arg Asn Gly Glu Leu Val
 65                  70                  75                  80

Ile His Glu Lys Gly Phe Tyr Tyr Ile Tyr Ser Gln Thr Tyr Phe Arg
                 85                  90                  95

Phe Gln Glu Glu Ile Lys Glu Asn Thr Lys Asn Asp Lys Gln Met Val
            100                 105                 110

Gln Tyr Ile Tyr Lys Tyr Thr Ser Tyr Pro Asp Pro Ile Leu Leu Met
        115                 120                 125

Lys Ser Ala Arg Asn Ser Cys Trp Ser Lys Asp Ala Glu Tyr Gly Leu
    130                 135                 140

Tyr Ser Ile Tyr Gln Gly Gly Ile Phe Glu Leu Lys Glu Asn Asp Arg
145                 150                 155                 160

Ile Phe Val Ser Val Thr Asn Glu His Leu Ile Asp Met Asp His Glu
                165                 170                 175

Ala Ser Phe Phe Gly Ala Phe Leu Val Gly
            180                 185
```

<210> SEQ ID NO 15
<211> LENGTH: 7
<212> TYPE: PRT
<213> ORGANISM: Artificial Sequence

```
<220> FEATURE:
<223> OTHER INFORMATION: L-NGR peptide sequence

<400> SEQUENCE: 15

Gly Asn Gly Arg Ala His Ala
1               5
```